United States Patent [19]
Mori

[11] Patent Number: 4,626,065
[45] Date of Patent: Dec. 2, 1986

[54] LIGHT CONDUCTION APPARATUS UTILIZING INTERMITTENT ILLUMINATION APPLIED TO OPTICAL FIBERS FOR PHOTOSYNTHETIC REACTION

[76] Inventor: Kei Mori, 3-16-3-501, Kaminoge, Setagaya-ku, Tokyo, Japan

[21] Appl. No.: 463,088

[22] Filed: Feb. 2, 1983

[30] Foreign Application Priority Data

Feb. 5, 1982 [JP] Japan .................................. 57-17238

[51] Int. Cl.[4] ........................ G02B 6/26; F21V 7/04; A01G 7/00
[52] U.S. Cl. ........................ 350/96.15; 350/96.10; 350/172; 362/32; 362/35; 362/805; 47/1.4; 47/DIG. 6
[58] Field of Search ............ 362/805, 32, 35; 350/96.10, 96.15, 96.18, 96.19, 96.20, 171, 169, 172; 47/1 R, 1 A, 59, 60, 61, 62, 65, 1.4, 1.7, DIG. 6; 372/68

[56] References Cited

U.S. PATENT DOCUMENTS

| | | | |
|---|---|---|---|
| 2,815,607 | 12/1951 | Schroeder | 47/1.4 |
| 3,538,312 | 11/1970 | Genahr | 350/96.24 |
| 3,560,872 | 2/1971 | Heimann | 372/68 |
| 3,959,923 | 6/1976 | Selke | 47/1.4 |
| 4,078,169 | 3/1978 | Armstrong | 362/805 |
| 4,173,390 | 11/1979 | Kach | 350/96.18 |
| 4,176,908 | 12/1979 | Wagner | 350/96.15 |
| 4,302,069 | 11/1981 | Niemi | 350/96.1 |
| 4,447,118 | 5/1984 | Mulkey | 350/96.1 |

FOREIGN PATENT DOCUMENTS

| | | | |
|---|---|---|---|
| 54-34255 | 3/1979 | Japan | 350/96.2 |
| 55-106405 | 8/1980 | Japan | 350/96.1 |
| 56-19001 | 2/1981 | Japan | 350/96.15 |
| 56-109108 | 8/1981 | Japan | 350/96.10 |
| 56-167114 | 12/1981 | Japan | 350/96.18 |
| 2040490 | 8/1980 | United Kingdom | 350/96.19 |
| 2059621 | 4/1981 | United Kingdom | 350/96.19 |

OTHER PUBLICATIONS

Fredrickson et al., "Utilization of the Effects of Intermittent Illumination . . . ", Proceedings of the IBP/PP, 9/69, pp. 519–541.

*Primary Examiner*—William L. Sikes
*Assistant Examiner*—Brian M. Healy
*Attorney, Agent, or Firm*—Jordan and Hamburg

[57] ABSTRACT

A light conduction apparatus for photosynthetic reaction includes a rotatable light distributor which may be a transparent rod or disc. Converged light is guided by a solid or tubular light conducting member into the light distributor and routed along at least one optical path through the light distributor as far as a radiation surface of the latter. The light output from the radiation surface is supplied a moment to each of a number of light conducting rods, which lead to a confinement for photosynthesis, once for each full rotation of the light distributor. Thus, the confinement shares a single light source which can be small size for given dimensions of the confinement.

16 Claims, 11 Drawing Figures

LIGHT CONDUCTION APPARATUS UTILIZING INTERMITTENT ILLUMINATION APPLIED TO OPTICAL FIBERS FOR PHOTOSYNTHETIC REACTION

BACKGROUND OF THE INVENTION

The present invention relates to a light conduction apparatus which promotes effective distribution of light for the photosynthesis of various photosynthetic substances such as algae typified by chlorella or spirolina, photosynthetic bacteria, artificial photosynthetic substances such as callus, plants and mushroom.

Installations heretofore proposed for photosynthesis include those for culturing chlorella. As well known to the art, chlorella is cultured by photosynthetic reactions under the supply of light and carbon dioxide ($CO_2$) and it has been customary to continuously supply light to chlorella throughout a reaction process. However, detailed analysis of the photosynthesis of chlorella showed that one reaction cycle requires the supply of light only for a fragment of its period (about 10 $\mu$sec) and proceeds without light for the rest of the period (about 200 $\mu$sec); the supply of light is rather undesirable for an effective reaction except for the fragmental period.

Meanwhile, a light source for culturing chlorella has usually been constituted by a number of fluorescent lamps arranged in a reaction or culture bath. A culture medium is caused to flow through the gaps between the adjacent fluorescent lamps in the bath. This suffers from the drawbacks that the whole apparatus becomes bulky, that the power consumption is objectionable, and that a troublesome countermeasure is required against heat generation. To eliminate these drawbacks, I have proposed in various forms to arrange photoradiators at the ends of optical fibers and converge the sunlight or any desired artificial light into the optical fibers, for thereby utilizing the light radiated from the photoradiators as a light source for photosynthesis. Still, the installations with such photoradiators cannot be made larger in dimension without needing a larger number of photoradiators and, therefore, a larger amount of converged light. This in turn requires a larger device for converging the sunlight or artificial light into the optical fibers.

SUMMARY OF THE INVENTION

A light conduction apparatus for photosynthetic reaction embodying the present invention includes a first light conducting member for conducting light therethrough. The light is input to one end of the light conducting member and output at the other end. A plurality of circularly arranged second light conducting members conduct light therethrough which is input at one ends thereof to a confinement in which photosynthetic reactions are to occur. Rotatable light distributor means routes the light output from the other end of the first light conducting member to the second light conducting members along at least one optical path defined thereinside and distributes the light to each of the second light conducting members once for one full rotation thereof.

In accordance with the present invention, a light conduction apparatus for photosynthetic reaction includes a rotatable light distributor which may be a transparent rod or disc. Converged light is guided by a solid or tubular light conducting member into the light distributor and routed along at least one optical path through the light distributor as far as a radiation surface of the latter. The light output from the radiation surface is supplied a moment to each of a number of light conducting rods, which lead to a confinement for photosynthesis, once for one full rotation of the light distributor. Thus, the confinement shares a single light source which can be small size for given dimensions of the confinement.

It is an object of the present invention to provide a light conduction apparatus which causes photosynthetic reactions to occur effectively by intermittent supply of light to a reactant.

It is another object of the present invention to provide a light conduction apparatus which allows a predetermined capacity of light converging device to suffice for the illumination of larger scale installations for photosynthesis.

It is another object of the present invention to provide a generally improved light conduction apparatus for photosynthetic reaction.

Other objects, together with the foregoing, are attained in the embodiments described in the following description and illustrated in the accompanying drawings.

DESCRIPTION OF THE PREFERRED EMBODIMENTS

While the light conduction apparatus for photosynthetic reaction of the present invention is susceptible of numerous physical embodiments, depending upon the environment and requirements of use, substantial numbers of the herein shown and described embodiments have been made, tested and used, and all have performed in an eminently satisfactory manner.

Figure 1:
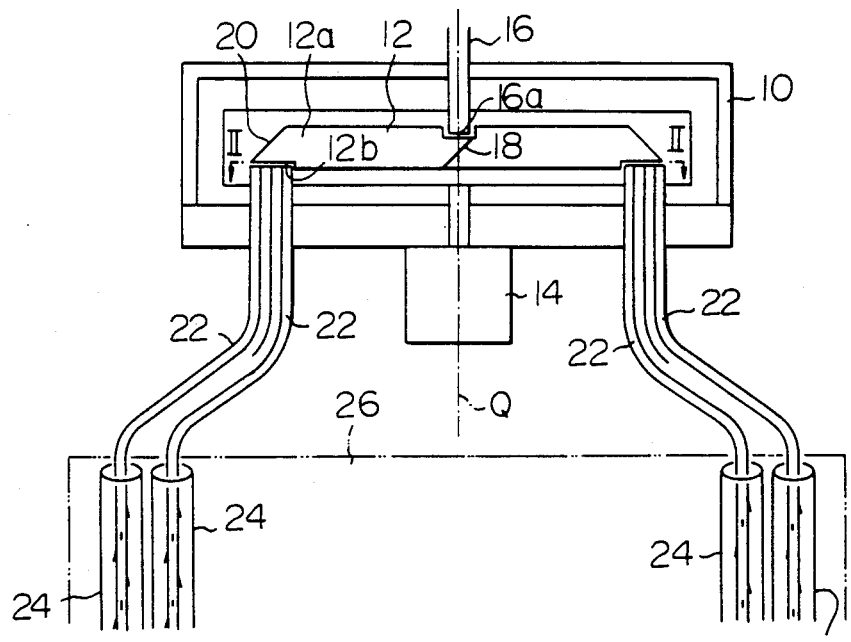
FIG. 1 is a sectional view of a light conduction apparatus embodying the present invention.

Referring to FIG. 1 of the drawings, a light conduction apparatus of the present invention comprises a frame or housing 10 which is fixed in place by suitable support means. A transparent light distributor 12 in the form of a rod is rotatably disposed in the frame 10 and held in driven connection with a motor 14, which is mounted on the bottom of the frame 10. The axis of rotation of the light distributor 12 is indicated by a phantom line Q. A solid or tubular light conducting member 16 extends into the frame 10 and has an axis which is aligned with the axis Q at its end 16$a$ adjacent to the light distributor 12. The light conductor 16 is adapted to transmit therethrough light which has been converged thereinto by a converging lens (not shown). The light applicable to the present invention may be the sunlight or any desired artificial light.

A mirror 18 is disposed in the light distributor 12 in alignment with the axis Q so as to steer the light output from the end 16a of the light conductor 16 toward an end portion 12a of the light distributor 12. A second mirror 20 is mounted in the end portion 12a of the light distributor 12, so that the light reflected by the mirror 18 will become incident on the mirror 20. The mirror 20 reflects the incident light toward the outside of the light distributor 12 through a radiation surface 12b.

Figure 2:
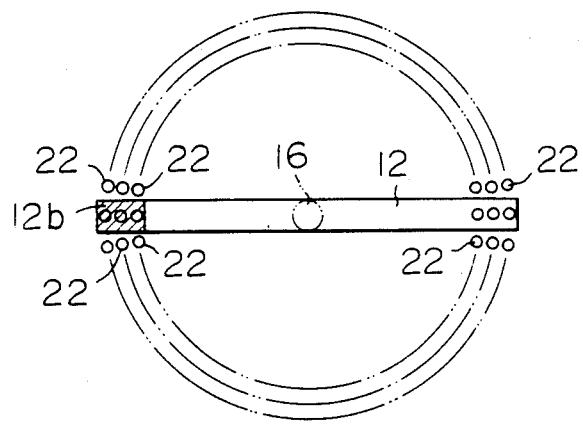
FIG. 2 is a section along line II—II of FIG. 1.

A number of light conducting members or rods 22 are fixedly arranged around the axis Q of rotation of the light distributor 12. As best shown in FIG. 2, the rods 22 are arranged such that the radiation surface 12b of the light distributor 12 successively moves past their upper or light input ends while in rotation about the axis Q. Each rod 22 extends from the frame 10 to a photoradiator 24 which is located in a reaction bath 26 for photosynthesis at a predetermined spacing from neighboring ones. It will be apparent that the reaction bath 26 is only illustrative and may be replaced by any other confinement such as an indoor plant growing garden. I have proposed photoradiators 24 in various forms as disclosed in Japanese Patent Application No. 56-109108/81, for example, and details thereof will not be described for the sake of simplicity.

In operation, the sunlight or desired artificial light propagated through the light conductor 16 is constantly reflected by the mirror 18 and then by the mirror 20 to come out the light distributor 12 through the radiation surface 12b. As the motor 14 is energized to rotate the light distributor 12 about the axis Q, the radiation surface 12b successively moves past the upper ends of the rods 22 which are arranged circularly around the axis Q. Each rod 22, therefore, is illuminated a moment once for one full rotation of the light distributor 12. The illumination time for each rod 22 may be about 10 $\mu$sec, for example. A photosynthetic substance in the bath 26 starts a photosynthetic reaction cycle around each rod 22 in response to the momentary supply of the light from the radiation surface 12a. The reaction cycle around the rod 22 proceeds while the light distributor 12 is rotating to distribute the light to the other rods 22. When the radiation surface 12a returns to the rod 22 concerned completing one full rotation, a second photosynthetic cycle begins in response to the resultant supply of the light. In this manner, photosynthesis continues effectively over the entire area of the reaction bath 26.

Thus, in accordance with the construction and arrangement shown in FIGS. 1 and 2, the light intensity above a lower limit necessary for photosynthesis can be insured merely by intensifying the light which reaches such a small area defined by the radiation surface 12b of the light distributor 12. This promotes a compact design of the device which is adapted to converge the natural or artificial light into the light conductor 16. Also, the sequential supply of the light to the number of light conducting rods 22 can cover a reaction bath having substantial dimensions.

Figure 3:
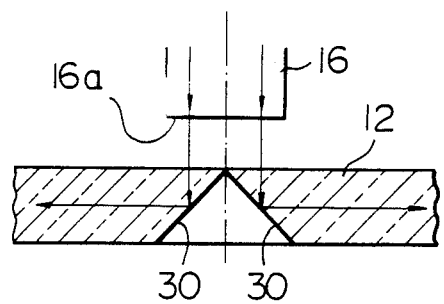
FIG. 3 is a fragmentary sectional side elevation of another embodiment of the present invention.

Referring to FIG. 3, another embodiment of the present invention is shown which will desirably function when the intensity of the light transmitted through the light conductor 16 is substantially high. In contrast to the single optical path in FIGS. 1 and 2 which leads from the mirror 18 to only one end of the light distributor 12, two optical paths extend away from each other to opposite ends of the light distributor 12 in the case of this alternative embodiment. As shown, two mirrors 30 are disposed in the light distributor 12 with their reflection surfaces oriented opposite to each other with respect to the axis Q of the light distributor 12. In this situation, the light output from the end 16a of the light conductor 16 will be reflected by the mirrors 30 to be routed along the two opposite paths toward opposite ends of the light distributor 12. It will be apparent in this case that the light distributor 12 is provided with the radiation surface 12b and mirror 20 at each end thereof. The double mirror arrangement is advantageous over the single mirror arrangement because it halves the required rotation speed of the distributor 12.

While the light distributor has been shown and described as taking the form of a rod, the rod may be replaced by a transparent disc as will be described with reference to FIGS. 4A and 4B. As shown, a light distributor 40 in the form of a transparent disc has a pyramid 42 at its axis Q whose reflection surface is oriented to reflect the incident light as indicated by arrows in FIG. 4B. Then, the light will be radiated at one location of the peripheral portion of the light distributor 40.

Figure 4A:
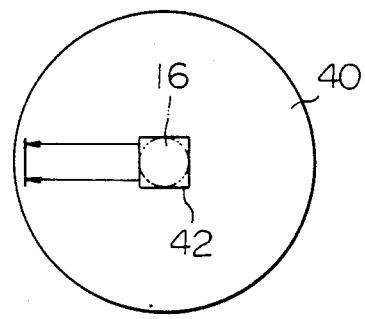
FIG. 4A is a fragmentary plan view of another embodiment of the present invention.
Figure 4B:
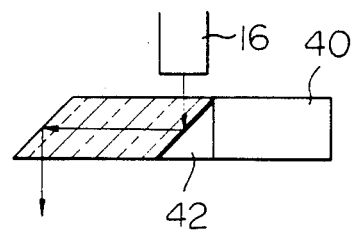
FIG. 4B is a sectional side elevation of a light distributor shown in FIG. 4A.
Figure 5A:
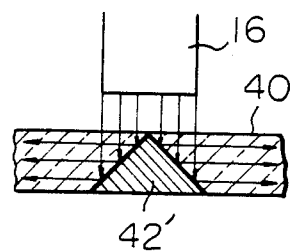
FIGS. 5A–5C are views of various modifications to the construction shown in FIGS. 4A and 4B.
Figure 5B:
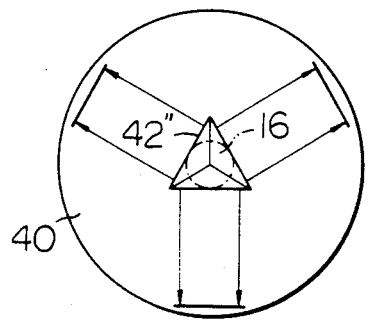
Figure 5C:
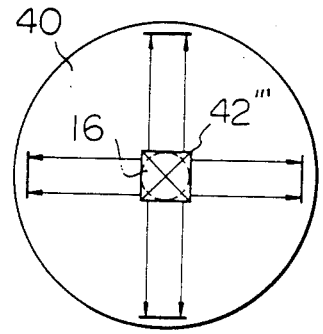

The configuration of the pyramid shown in FIGS. 4A and 4B is not limitative but may be replaced with any other desired pyramidal form. For example, a pyramid 42' shown in FIG. 5A has two reflection surfaces to steer the input light from the light conductor 16 to diametrically opposite peripheral portions of the light distributor 40. A pyramid 42'' shown in FIG. 5B has three reflection surfaces (triangular pyramid) which cause the input light to be redirected to three different peripheral portions of the light distributor 40. Further, a pyramid 42''' shown in FIG. 5C has four reflection surfaces (quadrangular pyramid) so that the input light is routed along four crosswise optical paths through the light distributor 40. Naturally, such different configurations of pyramids, inclusive of the pyramid shown in FIGS. 4A and 4B, may be selectively used on a single disc 40 in order to vary the amount and/or the frequency of illumination for each rod 22.

Figure 6:
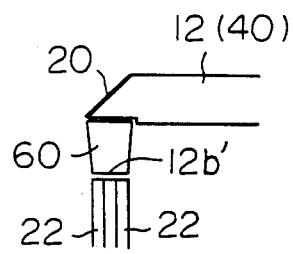
FIG. 6 is a fragmentary side elevation of another embodiment of the present invention.

As shown in FIG. 6, a pyramidal photocoupler 60 may be fixed to the radiation surface 12a of the light distributor 12 or 40. The photocoupler 60 will serve to more effectively guide the light output from the radiation surface 12a into the light conducting rods 22. In this case, a radiation surface 12b' is defined by the end of the photocoupler which faces the rods 22.

Figure 7A:
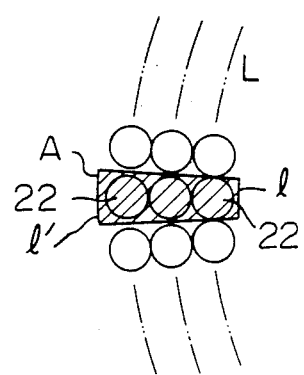
FIGS. 7A and 7B are enlarged plan views of different configurations of a light radiation surface.
Figure 7B:
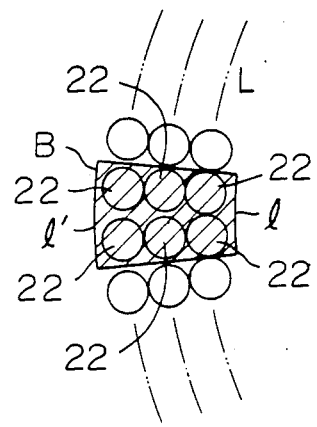

The radiation surface 12b of the light distributor or that 12b' of the photocoupler 60 has a sectorial shape which covers one row of radially aligned rods 22 at a time as indicated by a hatched area A in FIG. 7A, or a plurality of rows of radially aligned rods 22 at a time as indicated by a hatched area B in FIG. 7B. The radially innermost end l and outermost end l' of the sector A or B are formed arcuate to respectively coincide with the radially innermost and outermost ends of the annulus L which is defined by the rods 22. Thus, the light output from the radiation surface 12b or 12b' is allowed to become evenly incident on all the rods 22 which are simultaneously covered by the sector A or B.

In summary, it will be seen that the present invention provides a light conduction apparatus which promotes effective photosynthetic reactions and accommodates a larger reaction area for a given scale of a light source.

Various modifications will become possible for those skilled in the art after receiving the teachings of the present disclosure without departing from the scope thereof. For example, part of the photoradiators 24 constituted by the ends of the rods 22 may lead to one reaction bath and the rest to another reaction bath, instead of the single reaction bath shown and described.

What is claimed is:

1. A light conduction apparatus for photosynthesis reaction comprising a first rod member for conducting light therethrough, said first rod member having an input end portion for light input and an output end portion for light output, a plurality of second rod members for conducting light therethrough, each of said second rod members having an input end portion for light input, said second rod members conducting said light input to a confinement in which a photosynthetic reaction occurs, said input end portions of said second rod members being arranged along a circular array of concentric rows, rotatable light distributor means interposed between said outlet end portions of said first rod member and said input end portion of said second rod members, said light distributor means having a first portion disposed opposite said output end portion of said first rod member for receiving light from said first rod member, said light distributor means having a radiation surface spaced from said first portion and disposed opposite a portion of said circular array of said input end portions of said second rod members such that upon rotation of said light distribution means, said radiation surface successively passes over said input end portions of said second rod members to thereby sequentially route the light output from said outlet end portion of said first rod member successively to said circularly arrayed input end portions of said second rod members, and drive means for continuously rotating said rotatable light distributor means such that said rotatable light distributor means sequentially and successively distributes the light from said first rod member to said second rod members as said rotatable light distributor means is rotated by said drive means to thereby provide an intermittent supply of light to said confinement to cause said photosynthetic reactions to occur, said light distributor means comprising a transparent rod having said radiation surface formed at at least one end portion thereof, said transparent rod having an axis of rotation, said output end portion of said first rod member facing said axis of rotation of said transparent rod, said radiation surface of said light distributor means having a substantially rectangular shape and being positioned to sequentially move past said concentric rows of said input end portions of said second rod members while the transparent rod is rotated.

2. A light conduction apparatus for photosynthesis reaction comprising a first rod member for conducting light therethrough said first rod member having an input end portion for light input and an output end portion for light output, a plurality of second rod members for conducting light therethrough, each of said second rod members having an input end portion for light input, said second rod members conducting said light input to a confinement in which a photosynthetic reaction occurs, said input end portions of said second rod members being arranged along a circular array of concentric rows which are radially aligned, rotatable light distributor means interposed between said outlet end portion of said first rod member and said input end portion of said second rod members, said light distributor means having a first portion disposed opposite said output end portion of said first rod member for receiving light from said first rod member, said light distributor means having a radiation surface spaced from said first portion and disposed opposite a portion of said circular array of said input end portions of said second rod members such that upon rotation of said light distributor means, said radiation surface successively passes over said input end portion of said second rod members to thereby sequentially route the light output from said outlet end portion of said first rod member successively to said circularly arrayed input end portions of said second rod members, and drive means for continuously rotating said rotatable light distributor means such that said rotatable light distributor means sequentially and successively distributes the light from said first rod member to said second rod members as said rotatable light distributor means is rotated by said drive means to thereby provide an intermittent supply of light to said confinement for said photosynthetic reactions to occur, said light distributor means comprising a transparent disc having said radiation surface disposed at at least one radially outermost portion thereof, said disc having an axis of rotation, said output end portion of said first rod member facing said axis of rotation of said disc, said radiation surface of said light distributor means having a sectorial shape and being positioned to sequentially move past said radially aligned concentric rows of said one input end portion of said second rod members as said disc is rotated.

3. A light conduction apparatus as claimed in claim 1, wherein said transparent rod routes the light along at least one optical path in which the optical path extends from the axis of rotation of said transparent rod to said radiation surface.

4. A light conduction apparatus as claimed in claim 3, in which the optical path is defined by a mirror, said mirror having a reflective surface, said mirror being positioned in the transparent rod to face said output end portion of said first rod member at said reflection surface of said mirror.

5. A light conduction apparatus as claimed in claim 1, wherein there is a radiation surface on each opposite end portion of said transparent rod, said transparent rod routing the light along two optical paths in which the two said optical paths extend from said axis of rotation of said transparent rod away from each other to said radiation surfaces formed at said opposite end portions of said transparent rod, respectively.

6. A light conduction apparatus as claimed in claim 5, in which the optical paths are respectively defined by mirrors, said mirrors each having a reflective surface, said mirrors being positioned in said transparent rod to individually face said output end portion of said first rod member at said reflection surfaces of said mirrors.

7. A light conduction apparatus as claimed in claim 1, in which said input portions of said second rod members in each concentric row are radially aligned, said radiation surface covering a single row of said radially aligned input portions of said second rod members at a time.

8. A light conduction apparatus as claimed in claim 1, in which said radiation surface covers a plurality of said rows of radially aligned input portions of said second rod members at a time.

9. A light conduction apparatus as claimed in claim 2, wherein said disc routes the light along at least one optical path extends from said axis of rotation of the disc to said radiation surface.

10. A light conduction apparatus as claimed in claim 2, wherein said disc has two radiation surfaces formed at the radially outermost portions of said disc, and wherein there are a plurality of optical paths extending from said axis of rotation of said disc to said radiation surfaces formed at the radially outermost portions of said disc, respectively.

11. A light conduction apparatus as claimed in claim 2, in which said sectorial shape covers a single row of said radially aligned input end portions of said second rod members at a time.

12. A light conduction apparatus as claimed in claim 2, in which said sectorial shape covers a plurality of said rows of radially aligned input end portions of said second rod members at a time.

13. A light conduction apparatus as claimed in claim 2, in which said optical path is defined by a pyramid located in said disc to face said output end portion of said first rod member.

14. A light conduction apparatus as claimed in claim 13, in which said pyramid is replaceably disposed within said disc.

15. A light conduction apparatus as claimed in claim 1, in which the light input to said first rod member is sunlight.

16. A light conduction apparatus as claimed in claim 1, in which the light input to said first rod member is artificial light.

* * * * *